(12) United States Patent
Keith et al.

(10) Patent No.: US 7,881,156 B2
(45) Date of Patent: Feb. 1, 2011

(54) METHOD TO ESTIMATE TOWED ARRAY ANGLES

(75) Inventors: William L. Keith, Ashaway, RI (US); Kimberly M. Cipolla, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/806,262

(22) Filed: Jul. 9, 2010

(65) Prior Publication Data

US 2011/0002195 A1 Jan. 6, 2011

Related U.S. Application Data

(62) Division of application No. 12/133,896, filed on Jun. 5, 2008, now Pat. No. 7,782,712.

(51) Int. Cl.
*G01V 1/38* (2006.01)
(52) U.S. Cl. .................... 367/130; 367/20; 367/154
(58) Field of Classification Search ............ 367/19, 367/20, 129, 130, 154
See application file for complete search history.

(56) References Cited

U.S. PATENT DOCUMENTS

| 4,854,174 | A  | * | 8/1989  | Keith      | 73/714 |
| 6,111,817 | A  | * | 8/2000  | Teeter     | 367/13 |
| 6,341,532 | B1 | * | 1/2002  | Xu et al.  | 73/841 |
| 6,732,579 | B2 | * | 5/2004  | Keith et al. | 73/147 |
| 7,130,242 | B1 | * | 10/2006 | Keith et al. | 367/20 |

* cited by examiner

*Primary Examiner*—Ian J Lobo
(74) *Attorney, Agent, or Firm*—James M. Kasischke; Michael P. Stanley; Jean-Paul A. Nasser

(57) ABSTRACT

A towed array is provided with hot-film sensors and anemometer circuitry to calculate the angle of inclination of the towed array in real time during deployment of the towed array in a sea water environment. The hot-film sensors are arranged in pairs along the length of the towed array to increase the sensitivity of the inclination angle determinations and are located flush with an exterior surface of the towed array to minimize interference with the operation of the towed array. The pairs of hot-film sensors determine the local shear stresses on the towed array, and these measurements are converted to inclination angles using an empirically derived look-up table.

6 Claims, 3 Drawing Sheets

METHOD TO ESTIMATE TOWED ARRAY ANGLES

This is a divisional application and claims the benefit of the filing date of U.S. patent application Ser. No. 12/133,896; filed on Jun. 5, 2008 now U.S. Pat. No. 7,782,712 and allowed for issuance on Apr. 16, 2010 and entitled "A Method to Estimate Local Towed Array Angles Using Flush Mounted Hot Film Wall Shear Sensors" by the inventors, William L, Keith and Kimberly M. Cipolla.

STATEMENT OF GOVERNMENT INTEREST

The invention described herein may be manufactured and used by or for the Government of the United States of America for Governmental purposes without the payment of any royalties thereon or therefore.

BACKGROUND OF INVENTION

1) Field of the Invention

The present invention is directed to a method and system for estimating local towed array angles in order to improve acoustic beamforming during turns.

2) Description of Prior Art

Direction-finding devices are used to determine the direction of propagating signals and hence the location of the source of these signals. These devices are utilized in spectrum monitoring, reconnaissance and surveillance. Direction finders utilize arrangements or arrays of receivers to detect arriving signals and to determine the direction from which these signals originated. For example, appropriate time delays applied to the receivers serves to steer the array and to calculate the direction of arrival of the impinging signals. Therefore, the data gathered from the receivers are used in conjunction with data processing algorithms to interpret the data and determine signal propagation direction relative to the receivers.

When processing data from an array of acoustic sensors, accurate knowledge of the shape and location of the array is indispensable. For example, towed arrays suffer degraded detection and tracking capability during turns, partly due to imperfect knowledge of their shape, leading to erroneous beamformer shape correction. Software for predicting the shape of towed arrays as a function of time has been developed. The accuracy of these computational models is limited due to uncertainty in the drag coefficients for cases where the angle of tow is small-typically from zero to ten degrees. The ability to determine the local angles of an array at discrete locations along the array in real time is therefore highly advantageous.

For small angles, the turbulent boundary layer on the array undergoes structural changes, and the mean and fluctuating wall shear stress field at the fluid/solid interface changes. These changes are reflected in the space-time correlation coefficient of the wall shear stress field. A direct measurement of the space-time correlation function with pairs of wall shear stress sensors along the array therefore provides sufficient information to estimate the local angle of attack.

Currently, towed array heading sensors and depth sensors are used to estimate array shapes. The pms (position measurement system) for determining the relative positions of multi-line arrays is not suitable for use in a single array where small angles are involved. Pitot tubes or velocity probes are not practical due to mechanical constraints and incompatibility with the handling systems. Also, GPS sensors are not feasible due to the underwater application and operational depths. Lastly, real time computational models suffer from inaccuracy due to uncertainty in drag coefficients.

SUMMARY OF THE INVENTION

The present invention is directed to a method and system for estimating local towed array angles to improve acoustic beamforming during turns. In the invention, a flush mounted hot film sensor and an anemometry system are used to measure the mean and fluctuating turbulent wall shear stress in order to determine the local turbulent flow field characteristics associated with a long thin cylinder or towed array at a small angle to the mean flow. This small angle is typically less than about 10°. This measurement provides a real time estimation of the local angle of attack of a fleet towed array during a maneuver (i.e., a turn).

In one exemplary embodiment, the present invention is directed to a towed array having a tubular body with an interior, an exterior surface and a given length. This given length can be from about 100 meters to approximately 1000 meters.

In another embodiment, the towed array includes a plurality of tubular bodies arranged in parallel. Each tubular body in the plurality of tubular bodies includes a plurality of hot-film sensors. The towed array also includes a plurality of hydrophones disposed within the interior of the tubular body and spaced along the length of the tubular body.

In addition, a plurality of hot-film sensors is mounted on the tubular body flush with the exterior surface. The plurality of hot-film sensors is arranged in a plurality of groups spaced along the length of the tubular body, each group having at least two of the hot-film sensors.

In yet another embodiment, each group of hot-film sensors includes a pair of hot-film sensors, and the hot-film sensors in each pair are spaced along the length of the tubular body at a distance less than a turbulence correlation length for a turbulent boundary layer over the exterior surface of the tubular body. In one embodiment, the distance between hot-film sensors is less than three feet. Alternatively, the distance between hot-film sensors is from approximately 0.1 inches to approximately 4 inches.

In yet another embodiment, each hot-film sensor is rectangular and includes a long axis and a short axis perpendicular to the long axis. The long axis is arranged perpendicular to a tubular body axis running along the length of the tubular body. The towed array also includes a plurality of anemometer circuits provided such that each anemometer circuit is in communication with one of the hot-film sensors. In yet another embodiment, the towed array also includes at least one roll sensor disposed within the interior of the tubular body to detect rotation of the tubular body about a tubular body axis running along the length of the tubular body.

Another exemplary embodiment of the present invention is directed to a method for detecting an angle of inclination of a towed array. A plurality of hot-film sensors that are arranged in pairs and spaced along a length of a towed array of hydrophones deployed in sea water is used to determine mean wall shear stress at points along the length of the towed array corresponding to locations of the hot-film sensor pairs. The wall shear stresses are used to obtain an angle of inclination of the towed array at points corresponding to the locations of the hot-film sensor pairs. In one embodiment, use of the hot-film sensors to determine the mean wall shear stress includes computing the root mean square of voltage fluctuations at each hot-film sensor. In one embodiment, cross statistical voltage fluctuations are computed for each pair of hot-film sensors. In order to use the wall shear stresses to obtain the angles of inclination, an empirically derived look-up table containing correlations between wall shear stresses and angles of inclination is used. In one embodiment, roll sensors are used to provide compensation in obtaining the angle of inclination for rolling of the towed array about a towed array axis running along the length of the towed array.

In order to use the hot-film sensors, the plurality of hot-film sensors are mounted flush with an exterior surface of a tubular body of the towed array. The hot-film sensors in each pair of hot-film sensors are separated along the length of the tubular body by a distance less than a turbulence correlation length for a turbulent boundary layer over the exterior surface of the tubular body. In one embodiment, each hot-film sensor is rectangular, having a long axis and a short axis perpendicular to the long axis. The long axis is arranged perpendicular to an axis running along the length of the towed array.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

The present invention is directed to a method for estimating local towed array angles to improve acoustic beamforming during turns.

In one embodiment, a flush mounted hot film sensor and anemometry system that measures the mean and fluctuating turbulent wall shear stress is used to determine the local turbulent flow field characteristics associated with a long thin cylindrical body or a towed array at a small angle to the mean flow. This small angle is typically less than about 10°.

This measurement provides a real time estimation of the local angle of attack of a towed array during a maneuver (i.e., a turn) as the decrease in towing speed necessitated by certain maneuvers can cause the towed array to fall or sink. Suitable flush mounted hot film sensors and anemometry systems are known and available to those skilled in the art.

Exemplary embodiments of systems and methods in accordance with the present invention determine the shape of a towed array of sensors during maneuvers that involve turning the array. Determining the towed array shape provides for the tracking of targets using the array during turns. The present invention also provides for predicting the shape of arrays deployed by maneuvering Unmanned Undersea Vehicles (UUVs) or other platforms. In general, a towed array is towed behind a submarine or surface ship. When not deployed, the towed array is wound on a reel for storage.

Figure 1:
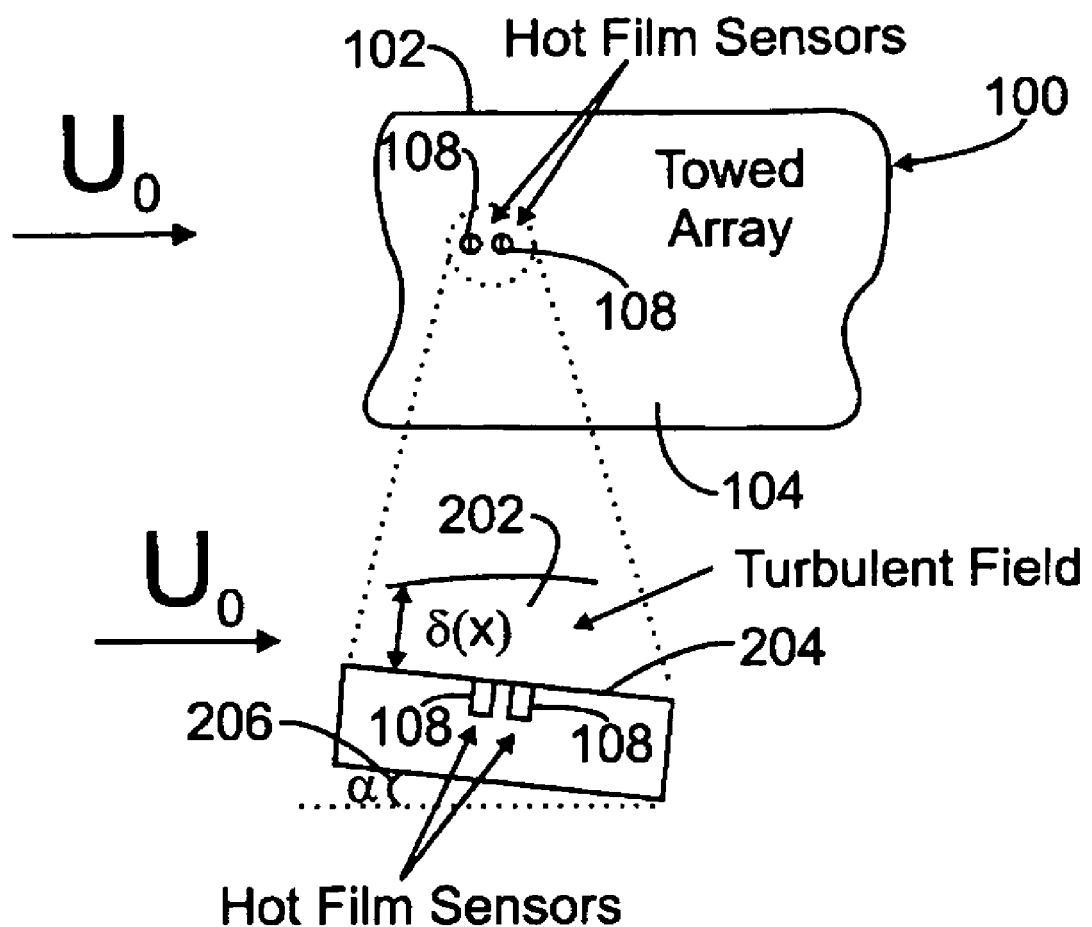
FIG. 1 is a schematic representation of an embodiment of flush mounted hot film sensors to measure local towed array angle of attack in accordance with the present invention.

Referring initially to FIG. 1, an exemplary embodiment of a towed array 100 in accordance with the present invention is illustrated. The towed array 100 includes a body 102 that is cylindrical or tubular in shape and includes a fluid-filled interior, an exterior surface 104 and a given length. Suitable lengths for the tubular body 102 are approximately 100 meters to approximately 1000 meters. The tubular body 102 is generally constructed of elastomeric material such as rubber.

Disposed within the fluid-filled interior of the tubular body 102 is a plurality of receivers (not shown) that are spaced from each other along the length of the towed array. Any number of receivers can be included in the array. The receivers are selected to be able to detect the desired type of incident signal. Suitable receivers include, but are not limited to, acoustic receivers, hydrophones, radar receivers, microwave receivers and combinations thereof.

Figure 2:
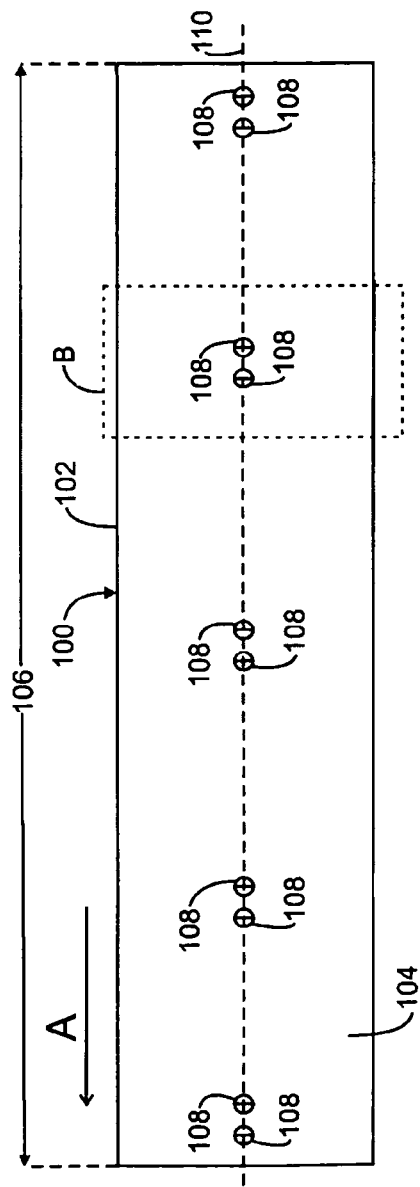
FIG. 2 is a schematic representation of an embodiment of the top of a towed array containing hot-film sensors in accordance with the present invention.

In one embodiment, a plurality of hydrophones is disposed within the interior of the tubular body and spaced along the length of the tubular body 102. The towed array 100 is pulled through water (i.e. sea water) in direction arrow A (See FIG. 2). In one embodiment, the towed array 100 includes a plurality of tubular bodies that are arranged in parallel, in series or in combinations of parallel and serial arrangements. Each tubular body 102 in the towed array 100 can include the features as discussed herein including a plurality of hot-film sensors 108.

The hot-film sensors 108 are mounted on the tubular body 102 flush with an exterior surface 104 of the tubular body. Suitable hot-film sensors are known and available in the art. The sensors are non-intrusive to the flow field, and there is no measurable effect of upstream sensors on those downstream. In one embodiment, each hot-film sensor 108 is arranged as a cylinder embedded into the material of the tubular body 102 with the end of the cylinder aligned flush with the exterior surface of the tubular body (See FIG. 1). Alternatively, the hot-film sensors 108, either alone or in groups or pairs, are incorporated into sub-assemblies such as straps or saddles that are attached or bonded to the exterior surface of the tubular body 102. Since in one embodiment the towed array 100 is a hollow, generally flexible tube that contains the hydrophones and is filled with fluid, arrangements of hot-film sensors that do not break the wall integrity of the tubular body 102 are preferred. In addition, it is preferred that the hot-film sensors 108 do not interfere with the ability of the towed array 100 to be wound on a reel.

In yet another embodiment, the hot-film sensors 108 are spaced along the length of the tubular body 102. Preferably, the hot-film sensors 108 are disposed in a line parallel to an axis 110 of the tubular body 102 that runs along the length of the tubular body and is generally parallel to the direction in which the towed array 100 is moving (i.e., arrow A). When deployed, the hot-film sensors 108 are preferably located along the top 204 (FIG. 3) of the tubular body 102 to facilitate the determination of an angle of inclination 206. However, the hot-film sensors 108 may be located at any circumferential position on the towed array 100 and still function for the purposes as described herein.

In one embodiment, single hot-film sensors are disposed along the length of the tubular body. Preferably, the hot-film sensors 108 are arranged in a plurality of groups, each group containing at least two of the hot-film sensors. The groups represent clusters of hot-film sensors, and the various groups are spaced from each other along the length of the tubular body 102. Preferably, each group includes a pair of hot-film sensors 108. The use of closely clustered groups or pairs of hot-film sensors 108 increases the resolution or sensitivity of the inclination angle measurements. In general, the total number of hot-film sensors 108, the number of groups and the arrangement of groups along the length of the tubular body 102 are determined based on the resolution desired in the calculated shaped of the deployed towed array 100 and the physical constraints of incorporating the hot-film sensors 108 and associated wiring into the towed array 100. For a towed array that maintains a linear or straight shape along an entire length, a single hot-film sensor or a single pair of hot-film sensors can be used to determine the angle of inclination for an entire towed array, because the local angle of inclination will be the same at any point along the length of the towed array 100. However, the towed array 100 is constructed of an elastomeric material and is capable of being wound on a reel.

In addition, the density of the towed array 100 may not be perfectly uniform along the length. Therefore, the tubular body of the towed array can form a curved or arched shaped along its 100 to 1000 meter length. The local angle of inclination could therefore vary along the length of the curved towed array. Therefore, hot-film sensors are needed at various locations along the length of the towed array. The local angles of inclination derived from each hot-film sensor are used to develop an overall profile or shape for the towed array. Increasing the number of hot-film sensors or sensor pairs increases the accuracy or resolution of the shape profile obtained.

In one embodiment, the towed array 100 includes a plurality of anemometer circuits (not shown). Each anemometer circuit is in communication with one of the hot film sensors. Suitable anemometer circuits are known to those skilled in the art and are commercially available.

As is also known in the art, the anemometers work in conjunction with the hot-film sensors 108 to operate the hot-film sensors at a constant temperature or resistance by adjusting the voltage applied to the associated hot-film sensor. The mean and fluctuating voltage levels from the anemometer are used to determine the local mean wall shear stress, also referred to as the local skin friction, caused within a turbulent boundary layer 202 on the surface of the towed array 100 in an area adjacent to the hot-film sensor. The mean and fluctuating wall shear stress is used to determine the local angle of inclination for example by using look-up tables. Each hot-film sensor 108 or combination of hot-film sensor and anemometer is connected to a data acquisition and analysis system. In one embodiment, one data acquisition system is provided per pair of hot-film sensors.

Figure 3:
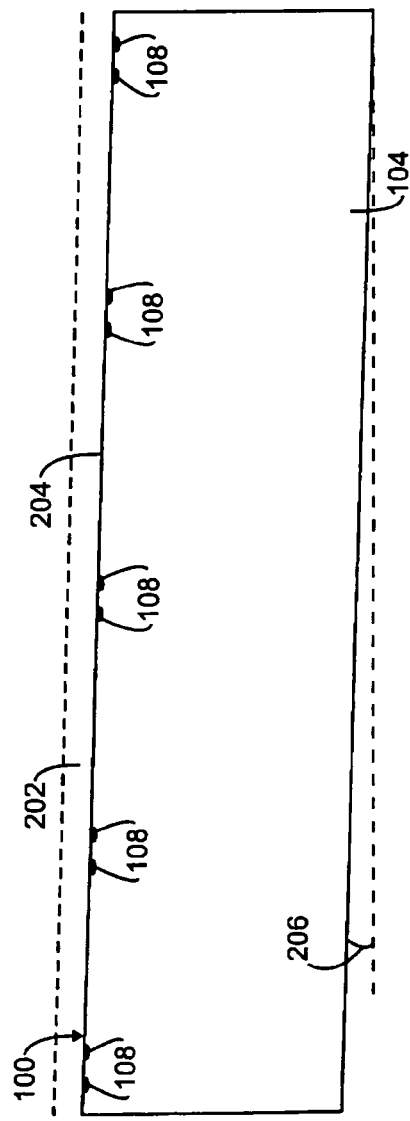
FIG. 3 is a schematic representation of a side view of the towed array embodiment of FIG. 2 with the view taken from section lines 2-2.
Figure 4:
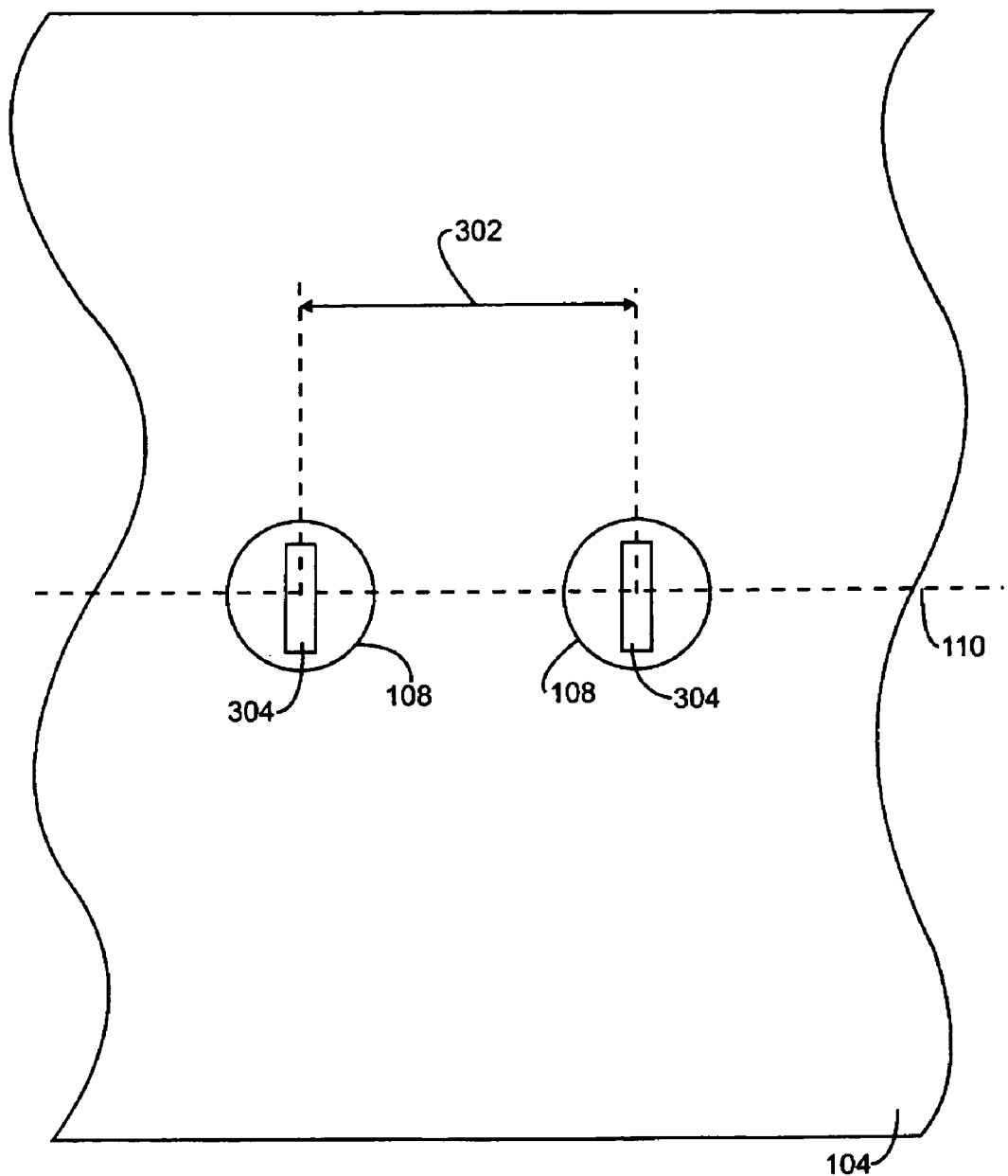
FIG. 4 is a view of section B of FIG. 3.

Referring now to FIG. 3 and FIG. 4, one embodiment is shown where each group of hot-film sensors includes a pair of hot-film sensors, the hot-film sensors 108 in each pair are spaced from each other along the length of the tubular body. A distance 302 between the pair of hot-film sensors 108 is within the distance over which the fluctuating wall shear stress has significant correlation at a specific Reynolds number. The distance over which the wall shear stress has significant correlation is directly related to the convection and decay of turbulent structures within the boundary layer developed over the towed body. In one embodiment, this distance between the hot-film sensors 108 is less than three feet. In another embodiment, this distance between hot-film sensors 108 is approximately 0.1 inches to approximately 4 inches. As is known in the art, the hot film sensor 108 includes a very thin conducting, e.g., metal, film 304 adhered to a substrate. Suitable metal films include platinum, and suitable substrates include ceramics or quartz. Gold plating can be applied to the ends of the rod for protection and support. The thickness of the conducting film is less than about 1000 Å. In one embodiment, each hot-film sensor 108 and in particular the conducting film portion of the hot-film sensor is rectangular and has a long axis and a short axis perpendicular to the long axis. The long axis is arranged perpendicular to the tubular body axis 110 running along the length of the tubular body.

In yet another embodiment, the towed array 100 also includes at least one roll sensor (not shown) disposed within the interior of the tubular body 102. In one embodiment, a plurality of roll sensors is provided. Suitable roll sensors are known and available in the art. The roll sensors are used to detect rotation of the tubular body about a tubular body axis running along the length of the tubular body. Knowledge of the roll is used to determine the orientation of the hot-film sensors about the circumference of the tubular member of the towed array. This information can be used to adjust the determination of the local angle of inclination based on the measured wall shear stress especially as the location of the hot-film sensor deviates from the top of the tubular body. In one embodiment, roll sensor measurements are incorporated into the look-up table used to derive inclination angles from wall shear stress measurements.

The present invention is also directed to methods for detecting an angle of inclination of a towed array. In one embodiment, the plurality of hot-film sensors that are arranged in pairs and spaced along the length of the towed array of hydrophones are used to determine the mean wall shear stress at points along the length of the towed array corresponding to locations of the hot-film sensor pairs. The towed array is deployed behind a surface vessel or submarine in a sea or ocean environment. The wall shear stress values are used to obtain an angle of inclination of the towed array at points corresponding to the locations of the hot-film sensor pairs. In one embodiment, using the hot-film sensors to determine the mean wall shear stress includes computing the root mean square of voltage fluctuations of each hot-film sensor. Two sensors arranged in pairs in close proximity to each other provide for increased accuracy in calculating the wall shear stress by using the voltage outputs to compute cross correlation functions and cross-spectra. Look up tables are then used to obtain estimates of the angle of inclination.

In yet another embodiment, roll sensors are used to provide compensation for rolling of the towed array (and the related change in the circumferential location of the shear stress sensors) about a towed array axis running along the length of the towed array in obtaining the angle of inclination.

In order to obtain the necessary wall shear stress measurements, the plurality of hot-film sensors are mounted on the towed array flush with an exterior surface of the tubular body of the towed array. The hot-film sensors that constitute each pair are separated along the length of the tubular body by a distance less than a turbulence correlation length for water flowing over the exterior surface of the tubular body. The spacing between the two sensors in each pair is determined by the thickness of the turbulent boundary layer on the array, which depends on the operational ship speed. In one embodiment, each hot-film sensor is rectangular with a long axis and a short axis perpendicular to the long axis and the long axis is arranged perpendicular to an axis running along the length of the towed array.

Systems and methods in accordance with the present invention can be used with both single and multi-line towed arrays. The hot film sensors generate no acoustic noise and are entirely passive.

An advantage of the hot film sensor systems is the ability to measure a quantity which depends explicitly on the actual turbulent flow field, which provides an unambiguous estimate of the local angle of the towed array 100 to the mean flow. The flush mounted sensors of the present invention are not sensitive to acoustic waves and, therefore, are not dependent upon local acoustic noise. Potential noise sources for hot films include ship wake and ambient ocean turbulence. However, tow cables are generally used to position the array far from the ship and any wake caused by the ship. The turbulent length scales due to ocean turbulence are generally much larger than those for the turbulent boundary layer, which exists on the array. Therefore, the effect of ocean turbulence on the measured correlation function will be qualitatively different than the effects of angle of attack which are of interest.

It will be understood that many additional changes in details, materials, steps, and arrangements of parts which have been described herein and illustrated in order to explain the nature of the invention, may be made by those skilled in the art within the principle and scope of the invention as expressed in the appended claims.

What is claimed is:

1. A method for detecting an angle of inclination of a towed array, the method comprising the steps of:

deploying a towed array of hydrophones;

providing a plurality of hot-film sensors, arranged in a plurality of groups spaced along a length of the towed array of hydrophones with each of the groups disposed in alignment with each other and with each group of the plurality of groups comprising at least two of the hot-film sensors with the distance between the hot-film sensors being less than three feet;

providing a plurality of anemometer circuits;

establishing communication with each anemometer circuit of the plurality of the anemometer circuits to one of the hot-film sensors of the plurality of hot-film sensors;

activating designated anemometer circuits of the plurality of anemometer circuits for designated hot-film sensors of the plurality of hot-film sensors;

adjusting a voltage of each of the designated hot-film sensors;

determining, in response to said adjusting step, mean wall shear stress at points along the length of the towed array corresponding to locations of the designated hot-film sensors; and determining, with the wall shear stresses, the angle of inclination of the towed array at points corresponding to the locations of the designated hot-film sensor wherein the alignment of the groups of hot-film sensors facilitates said determining the angle of inclination.

2. The method of claim 1, wherein said step of adjusting the voltage further comprises the step of computing the root mean square of voltage fluctuations at each designated hot-film sensor.

3. The method of claim 1, wherein said step of adjusting the voltage further comprises the step of computing cross statistical mean voltage fluctuations between designated hot-film sensors.

4. The method of claim 1, wherein said step of determining the angle of inclination further comprises the step of using an empirically derived look-up table comprising correlations between wall shear stresses and angles of inclination.

5. The method of claim 1, further comprising the step of using roll sensors to provide compensation in obtaining the angle of inclination for rolling of the towed array about a towed array axis running along the length of the towed array.

6. The method of claim 1, wherein each hot-film sensor is rectangular and comprises a long axis and a short axis perpendicular to the long axis, and said method further comprises the step of arranging the long axis perpendicular to an axis running along the length of the towed array.

* * * * *